(12) United States Patent
Kim et al.

(10) Patent No.: US 11,448,658 B2
(45) Date of Patent: Sep. 20, 2022

(54) METHOD AND DEVICE FOR CONTROLLING DETECTION-COMPOSITION PREPARATION INSTRUMENT

(71) Applicant: SEEGENE, INC., Seoul (KR)

(72) Inventors: Seong-Su Kim, Uijeongbu-si (KR); Na-Young Ji, Hwaseong-si (KR); Kyung-Hyun Min, Guri-si (KR)

(73) Assignee: SEEGENE, INC., Seoul (KR)

( * ) Notice: Subject to any disclaimer, the term of this patent is extended or adjusted under 35 U.S.C. 154(b) by 369 days.

(21) Appl. No.: 16/625,825

(22) PCT Filed: Jun. 29, 2018

(86) PCT No.: PCT/KR2018/007392
§ 371 (c)(1),
(2) Date: Dec. 23, 2019

(87) PCT Pub. No.: WO2019/004769
PCT Pub. Date: Jan. 3, 2019

(65) Prior Publication Data
US 2021/0156876 A1    May 27, 2021

(30) Foreign Application Priority Data
Jun. 29, 2017 (KR) .................. 10-2017-0082664

(51) Int. Cl.
*G01N 35/00* (2006.01)
*G01N 35/10* (2006.01)
(Continued)

(52) U.S. Cl.
CPC ..... *G01N 35/0092* (2013.01); *G01N 35/1009* (2013.01); *G05B 19/4155* (2013.01); *C12Q 1/6844* (2013.01)

(58) Field of Classification Search
CPC .. C12Q 1/6844; G05B 19/4155; G05B 11/01; G16B 30/00; G01N 35/0092;
(Continued)

(56) References Cited

U.S. PATENT DOCUMENTS 6,326,147 B1    12/2001   Oldham et al.
9,727,032 B2 *   8/2017   Subramaniam ........ G05B 11/01
(Continued)

FOREIGN PATENT DOCUMENTS

JP    2011-232260 A    11/2011
JP    2015-536643 A    12/2015
(Continued)

OTHER PUBLICATIONS

International Search Report and Written Opinion issued in PCT/KR2018/007392, dated Sep. 28, 2018; ISA/KR.
(Continued)

*Primary Examiner* — Shogo Sasaki
(74) *Attorney, Agent, or Firm* — Harness, Dickey & Pierce, P.L.C.

(57) ABSTRACT

Provided is a method and device for controlling a preparation instrument that prepares a detection composition used for detecting a target nucleic acid molecule in a specimen using an integrated instruction file.

20 Claims, 6 Drawing Sheets

(51) Int. Cl.
*G05B 19/4155* (2006.01)
*C12Q 1/6844* (2018.01)

(58) Field of Classification Search
CPC ......... G01N 35/1009; G01N 35/00584; G01N 2035/0091; B24B 41/062; B24B 41/065; B24B 5/04
See application file for complete search history.

(56) References Cited

U.S. PATENT DOCUMENTS

| | | | |
|---|---|---|---|
| 10,146,909 B2* | 12/2018 | Dimov | G06T 7/0012 |
| 11,080,848 B2* | 8/2021 | Dimov | G16H 10/40 |
| 11,135,699 B2* | 10/2021 | Subramaniam | G16B 30/00 |
| 2002/0019679 A1 | 2/2002 | Okada et al. | |
| 2004/0259111 A1 | 12/2004 | Marlowe et al. | |
| 2011/0207624 A1* | 8/2011 | Shen | C12Q 1/6869 506/17 |
| 2011/0246084 A1* | 10/2011 | Ronaghi | G16B 30/00 702/20 |
| 2012/0270206 A1 | 10/2012 | Ginns et al. | |
| 2013/0043150 A1 | 2/2013 | Ohashi | |
| 2014/0094971 A1 | 4/2014 | Thieme et al. | |
| 2018/0104790 A1* | 4/2018 | Subramaniam | B24B 5/04 |

FOREIGN PATENT DOCUMENTS

| | | |
|---|---|---|
| KR | 2017-0051922 A | 5/2017 |
| WO | 2003-044217 A2 | 5/2003 |

OTHER PUBLICATIONS

Extended European Search Report for corresponding Application No. 18823058.5 dated Mar. 18, 2021 (9 Pages).

* cited by examiner

METHOD AND DEVICE FOR CONTROLLING DETECTION-COMPOSITION PREPARATION INSTRUMENT

TECHNICAL FIELD

The present disclosure relates to a method and device for controlling a detection-composition preparation instrument that uses an integrated work processing file.

BACKGROUND ART

A gene amplification test is an in-vitro diagnostic test that amplifies a specific gene so as to determine whether the gene exists. In order to execute the gene amplification test using various specimens obtained from various animals, plants, and the like as well as humans, a process of removing a substance that inhibits a gene amplification reaction from a biological sample, and extracting a nucleic acid may be required. The extracted nucleic acid is used to produce a reaction solution for amplification.

A detection-composition preparation work such as preparation of an extracted nucleic acid, preparation of a reaction solution for amplification, and the like was manually performed by experimenters in early days. However, due to inefficiency from the perspective of human errors, cost, time, and the like, demands for automatic preparation instruments (e.g., Liquid Handling Instruments) that automatically prepare a detection composition have gradually increased.

One method of controlling an automatic preparation instrument is a scheme of defining minimum unit actions which may be performed by the automatic preparation instrument, and proceeding with a desired work action using a combination of the unit actions.

For example, when the automatic preparation instrument uses a pipettor which is a solution dispenser, minimum basic actions may include an action of moving the pipettor to a pipette tip, an action of fixing the pipette tip to the pipettor, an action of moving the pipettor to which the pipette tip is fixed to a predetermined place, and an action of dipping the pipette tip into a container by a predetermined depth. Each action is defined as a unit action. Also, when grippers are used, several basic actions associated with holding and moving an object may be defined as unit actions, respectively. When a heater is used, an action of heating up for a predetermined period of time may be defined as a unit action.

When preparation work that is desired to be executed in the automatic preparation instrument is preparation of a nucleic acid extract, the automatic preparation instrument starts operation from an action of fractionating a specimen in a sample tube, an action of dispensing a cytolytic solution to the fractionated specimen, and an action of heating up, proceeds with a series of actions for isolating and purifying a nucleic acid, and finally performs an action of collecting the isolated nucleic acid.

When it is desired to perform one work action, the method may selectively combine required unit actions from among the defined unit actions such that the automatic preparation instrument may perform the desired work action.

According to the method of controlling the automatic preparation device, all the unit actions that may be provided by the automatic preparation instrument may be processed based on variables (unit action variables) indicating unit actions.

When a work action is desired to be performed, unit action variables required for the work action are selected and suitable variable values are allocated, whereby the variable values allocated for each work action may be processed according to the order of driving work actions, unit actions corresponding to the selected variable values may be driven, and the work action is performed.

A variable value may have various characteristics. For example, when a unit action variable corresponds to a unit action that performs movement to a predetermined location, the variable value thereof may be a value corresponding to the coordinates of a target location. When a unit action variable corresponds to a unit action for raising or lowering a pipettor to a predetermined height, the variable value thereof may be a value associated with a height. A variable value may be a value indicating whether a certain unit action variable is selected. A variable value may have various characteristics.

The actual operations of the automatic preparation instrument may be controlled via a "work processing file".

Generally, an operator of the automatic preparation instrument may write a management document including information required for each preparation work that the preparation instrument desires to perform.

The management document includes a work action required for preparing a desired detection composition, variables indicating unit actions included in each work action, and variable values, and the like. In order to execute a preparation work in the automatic preparation instrument, a programming work for executing the preparation work in the preparation instrument is performed with reference to the management document, and a "work processing file" is finally produced.

When the types of preparation works are different from each other, work actions required for the corresponding preparation works are different from each other. Accordingly, a "work processing file" may need to be produced for each type of preparation work.

Although the types of preparation works are the same as each other, some of required work actions may be different due to an additionally selected item. For example, in the case of performing a work of preparing a nucleic acid extract, some work actions may be different according to the type of specimen or the type of target nucleotide sequence. In this instance, a "work processing file" needs to be produced for each preparation work. Preparation works which are slightly different in the work actions may require "work processing files", respectively.

It is inefficient to produce a "work processing file" for each case even when some work actions are different. Also, the number of "work processing files" that need to be managed increases, which is also a drawback.

A work action may need to be deleted or added, or a unit action variable or a variable value required for executing a work action may need to be deleted, added, or modified. Even when types of preparation works are different and required work actions are different due to an additionally selected item, some work actions may be used in common. Particularly, when a common work action needs to be edited, it is inefficient to repeatedly perform the same work for each "work processing file". Also, when an original developer is absent, it is difficult for a new developer to efficiently provide maintenance thereof, whereby the amount of time required is increased.

Therefore, there is a desire for a method of efficiently producing and operating a "work processing file".

DISCLOSURE OF INVENTION

Technical Problem

The inventors have tried to improve a scheme of producing a work processing file that controls a preparation instrument, for each preparation work. Accordingly, the inventors have recognized that a preparation instrument may be efficiently controlled and various preparation works may be performed by using a work data file for each preparation work and an integrated instruction file.

Therefore, an aspect of the present disclosure is to provide a method of controlling a preparation instrument that prepares a detection composition used for detecting a target nucleic acid molecule in a specimen.

Another aspect of the present disclosure is to provide a device for controlling a preparation instrument that prepares a detection composition used for detecting a target nucleic acid molecule in a specimen.

Solution to Problem

In accordance with an aspect of the present disclosure, there is provided a method of controlling a preparation instrument which prepares a detection composition used for detecting a target nucleic acid molecule in a specimen, the method including: displaying a plurality of option fields including a type of detection composition and a type of target nucleic acid molecule desired to be detected on a display so as to determine a desired detection composition, wherein the detection composition includes a nucleic acid extract and a reaction solution for nucleic acid amplification; receiving user selection information from each of the plurality of option fields; determining a work data file based on the selection information, wherein the work data file includes a work list including time-series work actions required for preparing the nucleic acid extract and/or a work list including time-series work actions required for preparing the reaction solution for nucleic acid amplification, and includes instruction name information and instruction processing information used for implementing the work actions in the preparation instrument; searching for an instruction that matches the instruction name information allocated to a work action from an integrated instruction file, according to the order of the work actions included in the determined work data file, wherein the integrated instruction file includes all instructions used for implementing all work actions that are desired to be operated in the preparation instrument, and the instructions include instructions for moving a pipettor, which performs pipetting in the preparation instrument, upward and downward, leftward and rightward, and forward and backward, and for dispensing, aspirating, or transferring a liquid; and performing control such that the retrieved instructions are processed according to the instruction processing information and the work actions are implemented in the preparation instrument.

In the method of controlling the preparation instrument according to an embodiment of the present disclosure, the determining the work data file may include: generating and the work data file using the selection information and one or more management data files selected based on the selection information, wherein the management data files are classified and stored according to a type of detection composition and a type of target nucleic acid molecule, and include work actions included in the work data file required according to the selection information, and instruction name information and instruction processing information associated with each work action.

In the method of controlling the preparation instrument according to an embodiment of the present disclosure, the generating the work data file may include: generating the work data file by extracting some or all work actions included in a single management data file, or generating the work data file by extracting some or all work actions included in each of the two or more management data files and combining the extracted work actions.

In the method of controlling the preparation instrument according to an embodiment of the present disclosure, the instruction processing information may include: unit action variables indicating unit actions of work actions implemented by the retrieved instructions and variable values allocated to the unit action variables.

In the method of controlling the preparation instrument according to an embodiment of the present disclosure, each instruction in the integrated instruction file includes unit action variables defined for a corresponding instruction, the unit action variables indicate unit actions of a work action implemented by an instruction, and each instruction is processed using unit action variables of which variable values are provided according to the instruction processing information from among unit action variables defined for each instruction.

In the method of controlling the preparation instrument according to an embodiment of the present disclosure, at least one instructions in the integrated instruction file implements two or more work actions.

In the method of controlling the preparation instrument according to an embodiment of the present disclosure, unit action variables to be used from among unit action variables defined for the at least one instructions are set to be different, such that two or more work actions are implemented.

The method of controlling the preparation instrument according to an embodiment of the present disclosure, may further include: displaying, on the display, a work window for displaying or editing work actions included in the work data file before controlling the preparation instrument.

In the method of controlling the preparation instrument according to an embodiment of the present disclosure, when work is suspended while the preparation instrument operates, the method may further include displaying, on the display, a work window for displaying state information of the suspended work action or editing a subsequent work action.

The method of controlling the preparation instrument according to an embodiment of the present disclosure, may further include: generating a setting data file in which the selection information is recorded, wherein the selection information recorded in the setting data file is processed via interoperation with the integrated instruction file.

In accordance with an aspect of the present disclosure, there is provided a device for controlling a preparation instrument which prepares a detection composition used for detecting a target nucleic acid molecule in a specimen, the device including: a display, one or more processors, and a memory, wherein the processor is configured to perform: displaying a plurality of option fields including a type of detection composition and a type of target nucleic acid molecule desired to be detected on a display so as to determine a desired detection composition, wherein the detection composition includes a nucleic acid extract and a reaction solution for nucleic acid amplification; receiving user selection information from each of the plurality of option fields so as to determine a work data file based on the selection information, wherein the work data file includes a work list including time-series work actions required for preparing the nucleic acid extract and/or a work list including time-series work actions required for preparing the reaction solution for nucleic acid amplification, and includes instruction name information and instruction processing information used for implementing the work actions in the preparation instrument; searching for an instruction that matches the instruction name information allocated to a work action from an integrated instruction file, according to the order of the work actions included in the determined work data file, wherein the integrated instruction file includes all instructions used for implementing all work actions that are desired to be operated in the preparation instrument, and the instructions include instructions for moving a pipettor, which performs pipetting in the preparation instrument, upward and downward, leftward and rightward, and forward and backward, and for dispensing, aspirating, or transferring a liquid; and performing control such that the retrieved instructions are processed according to the instruction processing information and the work actions are implemented in the preparation instrument.

In the device for controlling the preparation instrument, the memory is configured to store a management data file including work actions included in a work data file required according to selection information, and instruction name information and instruction processing information associated with each work action, wherein the management data file is classified and stored according to the type of detection composition and the type of target nucleic acid molecule; and the processor is configured to generate the work data file using the selection information and one or more management data files selected based on the selection information and implements determining the work data file.

In the device for controlling the preparation instrument, the processor is configured to generate the work data file by extracting some or all work actions included in a single management data file, or generate the work data file by extracting some or all work actions included in each of the two or more management data files and combining the extracted work actions.

In the device for controlling the preparation instrument, the instruction processing information includes unit action variables indicating unit actions of work actions implemented by the retrieved instructions and variable values allocated to the unit action variables.

In the device for controlling the preparation instrument, each instruction in the integrated instruction file includes unit action variables defined for a corresponding instruction, the unit action variables indicate unit actions of a work action implemented by an instruction; and the processor is configured to process each instruction using unit action variables of which variable values are provided according to the instruction processing information from among unit action variables defined for each instruction.

In the device for controlling the preparation instrument, the processor is configured to enable at least one the instructions in the integrated instruction file to implement two or more work actions.

In the device for controlling the preparation instrument, the processor is configured to set unit action variables, which are to be used from among unit action variables defined for the at least one instructions, to be different, such that two or more work actions are implemented.

In the device for controlling the preparation instrument, the processor is configured to display, on the display, a work window for displaying or editing work actions included in the work data file before controlling the preparation instrument.

In the device for controlling the preparation instrument, when work is suspended while the preparation instrument operates, the processor is configured to display, on the display, a work window for displaying state information of the suspended work action or editing a subsequent work action.

In the device for controlling the preparation instrument, the processor is configured to generate a setting data file in which the selection information is recorded, and process the selection information recorded in the setting data file via interoperation with the integrated instruction file.

Advantageous Effects of Invention

The features and the advantages of the present disclosure are summarized as follows.

A method and device for controlling a detection-composition preparation instrument according to the present disclosure may produce a single integrated instruction file, instead of producing a work processing file for each preparation work, and may use the integrated instruction file via interoperation with a work data file, thereby efficiently and readily performing various preparation works required by users.

Also, when a work processing file exists for each preparation work, each work processing file may be edited to perform a management action, such as modification, deletion, adding, and the like, with respect to a common item. The present disclosure may operate a single integrated instruction file, and may use a work data file of which editing is readily performed, whereby efficiency of management may be improved.

The present disclosure may execute two or more work actions using a single instruction by controlling variable values provided to unit action variables allocated to the instruction, whereby an integrated instruction file may be efficiently produced and utilized.

MODE FOR THE INVENTION

Hereinafter, the present disclosure will be described in detail with reference to embodiments. The embodiments are provided in order to more concretely describe the present disclosure. It is apparent to those skilled in the art that the scope of the present disclosure according to the subject matter of the present disclosure is not limited to the embodiments.

Embodiment

Figure 1:
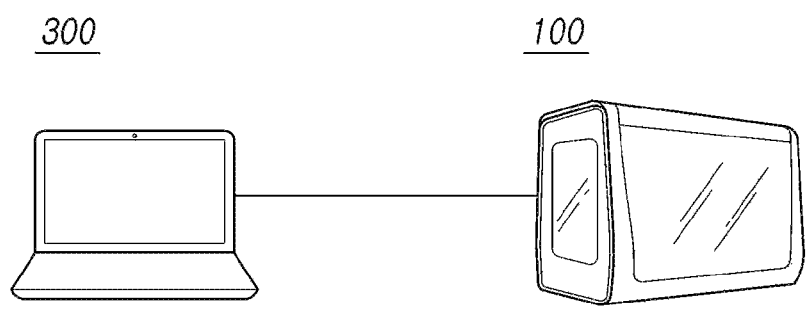
FIG. 1 is a diagram illustrating a detection-composition preparation system according to the present disclosure.

FIG. 1 is a diagram illustrating a detection-composition preparation instrument 100 and a preparation instrument control device 300 according to an embodiment of the present disclosure. Referring to FIG. 1, a detection-composition preparation system includes the detection-composition preparation instrument 100 and the preparation instrument control device 300 that controls the preparation instrument. In the detection-composition preparation system, the detection-composition preparation instrument 100 automatically performs a process of preparing a detection composition used for detecting a target nucleotide sequence in a specimen according to a control signal of the preparation instrument control device 300.

In the present disclosure, the detection-composition preparation process includes a process of extracting a nucleic acid from a specimen, a process of producing a reaction solution for polymerase chain reaction (PCR), and a process that combines extracting a nucleic acid and producing a reaction solution for PCR.

The method (S200) of controlling the detection-composition preparation instrument 100 according to the present disclosure may be implemented by the preparation instrument control device 300, and the operation of each step may be controlled by each element of the preparation instrument control device 300.

Figure 3:
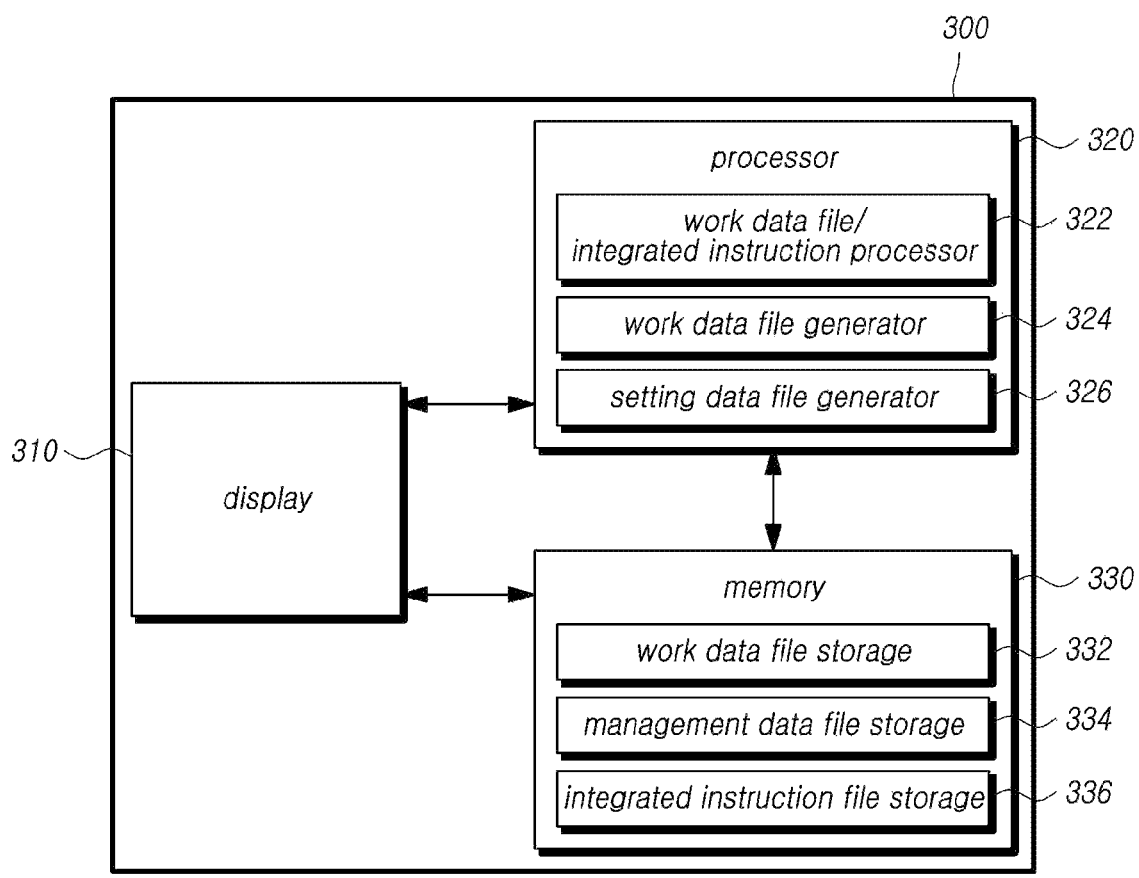
FIG. 3 is a diagram illustrating the whole of a device 300 for controlling a detection-composition preparation instrument according to the present disclosure.

The preparation instrument control device 300 according to the present disclosure may include a display 310, one or more processors 320, and a memory 330 that stores programs and/or data, as illustrated in FIG. 3.

In addition, although not illustrated in FIG. 3, the preparation instrument control device 300 may further include a permanent storage such as a disk drive or the like, a communication port communicating with an external device, and a user interface device such as a touch panel, a key, a button, and the like.

The preparation instrument control device 300 according to the present disclosure may be controlled based on software. The method of controlling the detection-composition preparation instrument 100 may be controlled by software according to the present disclosure. The methods implemented by software or algorithms are computer-readable codes or program instructions, which are executable by the processor 320, and may be stored in a computer-readable recording medium.

Here, the computer-readable recording medium may include a magnetic storage medium (e.g., a read-only memory (ROM), a random-access memory (RAM), a floppy disk, a hard disk, or the like), an optical-readable medium (e.g., a CD-ROM or a digital versatile disc (DVD), and the like. The computer-readable recording medium is distributed into computer systems connected to each other through a network, so that the computer-readable code can be stored and executed in a distribution scheme. The medium may be readable by a computer, may be stored in the memory 330, and may be executed in the processor 320.

The processor 320 may include parts, such as a work data file/integrated instruction file processor 322, a work data file generator 324, and a setting data file generator 326.

The memory 330 may include parts, such as a work data file storage 332, a management data file storage 334, and an integrated instruction file storage 336.

Each element is functionally distinguished in order to clearly describe the operation of the detection-composition preparation instrument control device 300 according to the present disclosure. Therefore, each part may not be necessarily distinguished as a single physically separate element. For example, each part may be implemented as a set of computer instructions of some of the programs. Alternatively, the function of a corresponding part may be implemented by an operation processing device as a program is executed. A separate storage may be used in order to distinguish the type of data that is stored.

Also, elements of the detection-composition preparation instrument control device 300 according to the present disclosure may be implemented as programs/applications executed by a single information-processing terminal, such as a user computer. Alternatively, some elements may be implemented by the terminal, and other elements may be implemented by the preparation instrument 100 that is connected with the terminal. Alternatively, the elements may be implemented as a set of logical circuits included in a semi-conductor processor.

The preparation instrument 100 implemented by the detection-composition preparation instrument control device 300 according to the present disclosure may be an automated liquid handling apparatus. The automated liquid handling apparatus may automatically and programmatically aspirate and/or dispense a desired amount of reagent, sample, or other liquid from/to a designated container, for the automation of chemical or biochemical experiment. Various configurations of the automated liquid handling apparatus have been known to those skilled in the art.

All of the elements of the preparation instrument 100 are designed as an integrated device, and are located in a housing.

A pipetting module that is capable of automatically moving upward, downward, leftward, rightward, forward, and backward is located above a deck of the automated preparation instrument 100. The pipetting module includes one or more pipettors which independently or dependently move and operate. A tip or a needle is coupled to the end of the pipettor, and is used for aspirating and dispensing a solution.

The preparation instrument 100 according to the present disclosure is, for example, a device made by Hamilton company located in Switzerland. For example, the preparation instrument 100 may be Hamilton STAR, Hamilton NIMBUS, Hamilton STARplus), and Hamilton STARlet.

Hereinafter, with reference to FIGS. 2 and 3, the operation of each step of the method (S200) of controlling a detection-composition preparation instrument according to the present disclosure, and each element of the preparation instrument control device 300 that controls the operation of each step will be described.

Figure 2:
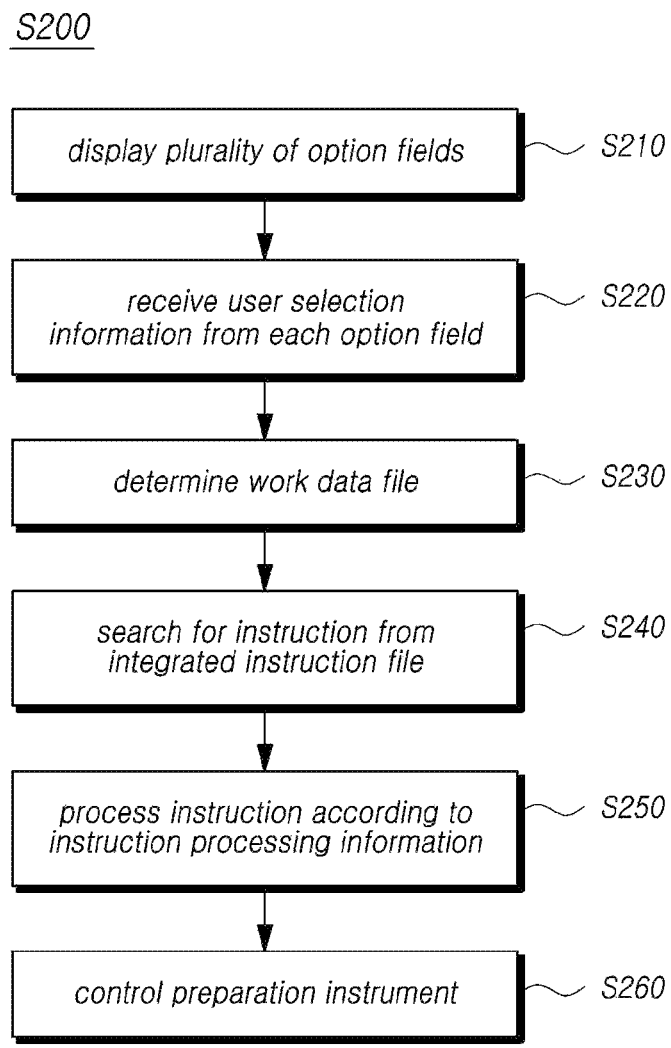
FIG. 2 is a flowchart illustrating a method (S200) of controlling a detection-composition preparation instrument according to the present disclosure.

FIG. 2 is a flowchart illustrating a method (S200) of controlling a detection-composition preparation instrument according to the present disclosure.

As illustrated in FIG. 2, the preparation instrument control device 300 specifies a desired detection composition in operation S210. To this end, the processor 320 of the preparation instrument control device 300 may display, on a display 310, a plurality of option fields for selecting options including the type of a detection composition and the type of a target nucleic acid molecule.

The detection composition includes a nucleic acid extract and a reaction solution for nucleic acid amplification (e.g., PCR reaction solution).

The preparation instrument 100 may perform a nucleic acid extract preparation work or a nucleic acid amplification reaction solution preparation work. Alternatively, the preparation instrument 100 may perform a preparation work in which a nucleic acid extract preparation work and a nucleic acid amplification reaction solution preparation work are performed at the same time.

The display 310 may be controlled by the processor 320, and may display data or images, such as the plurality of option fields stored in the memory 330.

The memory 330 may store programs or data for processing and controlling the processor 320 (e.g., a management data file, a work data file, and an integrated instruction file), and may store input/output data (e.g., user selection information associated with the plurality of option fields, selection information such as additional information that a user manually inputs via a barcode and an input device such as a mouse, and the like).

The memory 330 may include at least one type of storage medium from among a flash memory type, a hard disk type, a multimedia card micro type, a card type memory (e.g., an SD memory, an XD memory, or the like), a random access memory (RAM), a static RAM (SRAM), a read-only memory (ROM), an electrically erasable programmable ROM (EEPROM), a PROM, a magnetic memory, a magnetic disk, and an optical disk.

A user may be capable of inputting selection information with respect to the plurality of option fields displayed on the display 310. The display 310 may be implemented as a human interface device for enabling a user to select an option field, for example, a touch screen, a touch panel, or the like.

In operation S220, the processor 320 may receive user selection information input via the display 310. In this instance, the option fields may be provided variously according to a work that is to be prepared using the preparation instrument 100.

The processor 320 may display, on the display 310, a plurality of option fields for selecting a plurality of objects (e.g., the type of detection composition, the type of target nucleic acid molecule, a product for test, expendables, and the like) set for a detection-composition preparation work, and the list of a plurality of items given for each option field, whereby a user may select an item from each option field.

Also, the processor 320 may display, on the display 310, a setting window via which a character or a number is input, or information is input using an external input interface, whereby information may be set.

For example, tools for performing work for each type of detection composition, for example, barcode information of a container containing a nucleic acid extraction reagent (extraction kit) or a reagent required for PCR reaction solution (so called master mix), the number of cycles in which mixing is performed when the master mix is produced, the number of samples, the volume of liquid such as the reagent, the PCR reaction solution, and a sample, the number of positive controls (PC), negative controls (NC), or internal controls (IC) for identifying a problem in performing the work and verifying reliability, information indicating whether to use a clot monitoring function, and information indicating whether to use an anti-drop control (ADC) function, may be input as selection information in the option fields. Reagents and controls are contained in advance in the preparation instrument 100, and may be indicated as barcodes such that the preparation instrument 100 identifies the reagents and controls.

Some of the received selection information may be used for specifying work to be executed by the preparation instrument 100, and for selecting or generating a required work data file. Also, some of the received selection information may be used as information (e.g., a variable value) for performing logical determination or for controlling details of a device while a work is performed.

In operation S230, the processor 320 may determine a work data file from among work data files stored in the work data file storage 332 of the memory 330 according to the received selection information. Also, determining the work data file by the processor 320 may be executed by generating the work data file by the work data file generator 324 according to the received selection information.

The work data file includes a work list including time-series work actions required for nucleic acid extract preparation and/or a work list including time-series work actions required for nucleic acid amplification reaction solution preparation. Also, the work data file includes instruction name information and instruction processing information used for implementing the work actions included in the work list in the preparation instrument 100.

The time-series work actions include respective work actions implemented over time by the processor 320 in the preparation instrument 100.

Although not illustrated, the preparation instrument 100 of the present disclosure may include a nucleic acid extract reagent location, a nucleic acid amplification reagent location, a specimen location, a nucleic acid extract location, a nucleic acid extract location, a nucleic acid amplification reaction solution producer, and a pipetting part.

When a detection composition that the preparation instruction 100 desires to prepare is a nucleic acid extract, the preparation instrument 100 may control a pipettor of the pipetting part to perform a nucleic acid extract preparation work action according to an instruction, on a deck including a specimen location, a nucleic acid extract reagent location, and a nucleic acid extracting location or.

When the detection composition that the preparation instrument 100 desires to prepare is a PCR reaction, the preparation instrument 100 controls the pipettor of the pipetting part so as to perform a PCR reaction preparation work action according to an instruction on a deck including a PCR reagent location, a nucleic acid extract location, and a PCR reaction solution location.

The time-series work actions are listed in a work list in order of actual occurrence of work actions. Alternatively, time-series work actions may be listed in a work list in a different order from the order of actual occurrence of work actions. In this instance, when the work is performed by the processor, information via which the processor recognizes the order of work actions needs to be provided. For example, when work actions are listed in the work list, information indicating the order of execution of work actions is written together.

According to an embodiment of the present disclosure, a work data file includes a plurality of areas including unique information. More particularly, the work data file includes a first area to a third area.

The first area of the work data file includes work action information associated with a work list required for preparing a desired detection composition. In the first area, work actions for preparing the desired detection composition may be arranged in a time-serial manner according to the order of work actions executed in the preparation instrument 100.

For example, when a desired preparation work is extraction of a nucleic acid from a specimen, a work list may include detailed work actions in chronological order based on a lysis process, a bead binding process, and a washing process. More particularly, the lysis process may include work actions, such as dispensing Protenase K, dispensing an internal control (IC), moving a plate from a magnet to a heater, dispensing a lysis buffer, and dispensing a specimen. The work actions may be written as 'PK_Dispense', 'IC_Dispense', 'Move_DWP_from_Magnet_to_Heater_1', 'Lysis_Buffer_Dispense', and 'Sample_Dispense', respectively.

When a desired preparation work is a PCR reaction solution preparation work, a work list may include work actions, such as producing a master mix, dispensing the master mix to a tube, and dispensing an extracted nucleic acid to the tube. The work actions may be written as 'Build Master mix', 'Distribute Master mix to the tube', and 'Transfer extracted nucleic acid to the tube', respectively.

The information in the first area may be used for identifying a work action required for preparing a desired detection composition, and may be used for the processor 320 to provide a user with guidance associated with a work action that is currently executed in the display 310, when the identified work action is actually implemented in the preparation instrument 100.

The second area includes instruction name information associated with an instruction which is allocated to each work action so as to control the preparation instrument 100 and to perform each work action arranged in the first area.

The instruction may indicate an instruction which enables a work action to be executed in the preparation instrument 100. The instruction is used for actually controlling a work action executed in the preparation instrument 100, and may be included in the integrated instruction file storage 336.

In the present disclosure, a work processing file that actually controls a work action in a preparation instrument known to those skilled in the art is defined and used as an integrated instruction file for performing the technical idea of the present disclosure.

The instruction name information indicates at least one instructions included in the integrated instruction file so as to execute work actions of a work data file using the integrated instruction file, whereby two files are connected via the instruction name information and perform interaction.

For example, using the instruction name information in the work data file, the work data file may be connected to an instruction defined by the name in the integrated instruction file.

'Disp_PKmix' may be used as the instruction name for a work action of dispensing Protenase K included in the lysis process. 'Disp_IC' may be used for the instruction name for a work action of dispensing an internal control (IC). 'Move_DWP' may be used for the instruction name for a work action of moving a plate from a magnet to a heater. 'Disp_Buffer' may be used for the instruction name for a work action of dispensing a lysis buffer. 'Disp_Sample' may be used for the instruction name for a work action of dispensing a specimen.

The third area may include instruction processing information connected to the instruction name information of the second area.

The instruction processing information may include variables indicating unit actions included in a work action, and variable values allocated to the unit action variables.

A single work action may be implemented by combining a plurality of unit actions. For example, dispensing a specimen (Sample_Dispense), which is one of the work actions in the lysis process, may be implemented by a plurality of unit actions, such as an action of moving a solution dispenser to a specimen tube, an action of controlling a tip to be placed at a predetermined height from the bottom of the specimen tube, an action of aspirating a specimen from the specimen tube, an action of moving to a lysis plate, and the like.

Additional information may be required to execute each unit action. For example, the unit actions may require sample tube location information, height information associated with a height from the bottom of a sample tube when specimen aspirating is performed, and the volume of a specimen to be aspirated, and location information associated with a lysis plate.

The third area includes unit actions of a work action, and additional information associated with the unit actions, and provides required information when an instruction corresponding to the instruction name of the second area is executed among the integrated instruction file.

In the present disclosure, the unit actions may be indicated by unit action variables, and additional information required for implementing a unit action may be processed as a variable value. 'Start_Location' may be used as the variable name for an action of moving a solution dispenser to a specimen tube. 'Asp_Bottom_Height' may be used as the variable name for an action of controlling a tip to be placed at a predetermined height from the bottom of the specimen tube. 'Asp_position' may be used as the variable name for an action of aspirating a specimen from the specimen tube.

Representatively, a variable value is a numerical value. A work action may be implemented as a numerical value indicating the degree of implementation for a unit action corresponding to a unit action variable is read. A variable value may be a character.

A certain numerical value or a certain character may be used as information indicating that processing needs to be performed such that a unit action indicated by the corresponding unit action variable is not executed.

In a work data file, the information such as a work list, instruction name information and instruction processing information may be arranged in the X-axis and Y-axis. In this instance, in the X-axis, unit action variables indicating unit actions included in each of all work actions that are desired to be executed by the preparation instrument may be arranged. In the Y-axis, time-series work actions may be arranged. In this instance, in each piece of instruction processing information recorded in the X-axis for a corresponding work action arranged in the Y-axis, 0 or null may be recorded as variable values for the unit action variables remaining after excluding unit action variables corresponding to unit actions of each work action.

To arrange all possible unit action variables in the X-axis allows a user to readily edit unit action variables required for a work action without deleting or adding unit action variables in a work data file and to efficiently provide maintenance thereof.

In order to determine the work data file in operation S230, the processor 320 may call a work data file stored in the memory 330, or may generate a work data file by the work data file generator 324.

The processor 320 may store, in the memory 330, work data files for each of the works which can be combined based on selection information. When selection information input into an option field is received, the processor 320 may select a work data file that matches the selection information from the work data file storage 332, and may determine the selected work data file as the work data file.

There may be various combinations of selection information for option fields depending on a user when a preparation work is performed. Various work data files suitable for the various combinations of selection information may need to be provided.

Generally, in the case of a detection-composition preparation instrument, a work list of a preparation work may be determined almost based on a combination of the type of detection composition and the type of target nucleic acid molecule. That is, work actions of the work list may be determined based on the type of detection composition and the type of target nucleic acid molecule, and other selection information may act as information that is additionally required for performing a work action.

For example, when the types of detection composition which can be prepared are a "nucleic acid extract" and a "PCR reaction solution"; the types of target nucleic acid molecules are "respiratory infection microorganism panel 1 (RP1)" and "sexually transmitted disease microorganism panel 1 (STI P1)"; selectable sample racks are 32 Sample Rack, 5×12 Rack, and 5×18 Rack; and selectable sample labware are a 1.5 ml Tube, a 1.2 ml Tube, a 1.6 ml Tube, 1.5 ml & 1.2 ml Tubes, 1.5 ml Tube & 1.6 ml Tubes, 1.2 ml & 1.6 ml Tubes, and 1.5 ml & 1.2 ml & 1.6 ml Tubes, the types of the detection compositions which can be prepared and the types of target nucleic acid molecules may be taken into consideration when a work data file (particularly, a work list) is produced, but the sample racks or the sample labware may not be taken into consideration.

According to an embodiment, the present disclosure may produce work data files of desired work actions, based on the combination of the type of a detection composition and the type of target nucleic acid molecule among selection information.

According an embodiment, a work data file may be produced and classified based on the type of detection composition and the type of target nucleic acid molecule.

According to an embodiment, the number of work data files produced and classified is the same as the number of combinations of the number of types of desired detection compositions and the number of types of target nucleic acid molecules.

According to an embodiment, when desired detection compositions are the same, and the types of target nucleic acids are different, works associated with some target nucleic acid molecules may be performed based on the same work list. In this instance, a single work data file may be produced.

To perform a desired preparation work based on selection information, the processor 320 may generate a work data file by the work data file generator 324, and may provide the generated work data file.

In the present specification, the term "determining a work data file" includes an action of generating a work data file.

To generate a work data file by the work data file generator 324, the processor 320 may use a management data file stored in the management data file storage 334 of the memory 330.

The management data file includes work actions included in a work data file required based on selection information, and instruction name information and instruction processing information for each work action.

Also, the management data file basically includes information included in the work data file, and additionally includes information associated with an environment condition of a preparation instrument (e.g., a temperature, a barcode count (barcode_count), and a time range) and description information associated with each work action. That is, the management data file is a data file associated with a work data file, and may further include additional information in addition to the work data file.

The management data file may be also produced and classified based on the type of detection composition and the type of target nucleic acid molecule, in the same manner as a work data file. The management data file may be stored in the management data file storage 334.

The method (S200) of controlling the detection-composition preparation instrument according to the present disclosure may be implemented by the preparation instrument control device 300, and the operation of each step may be controlled by each element of the preparation instrument control device 300.

FIG. 4 is a diagram illustrating an example of generating a work data file from a management data file according to an embodiment of the present disclosure.

Figure 4A:
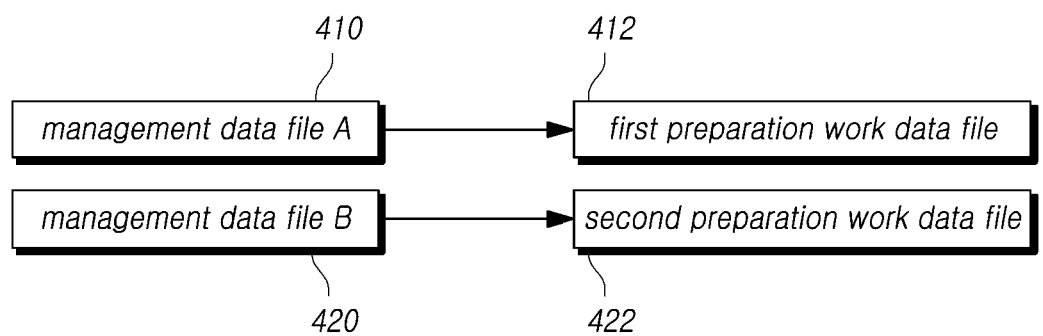
FIG. 4 is a diagram illustrating an example of generating a work data file from a management data file according to an embodiment of the present disclosure.

FIG. 4A is an example of generating a single preparation work data file 412 and 422 from a single management data file 410 and 420.

Figure 4B:
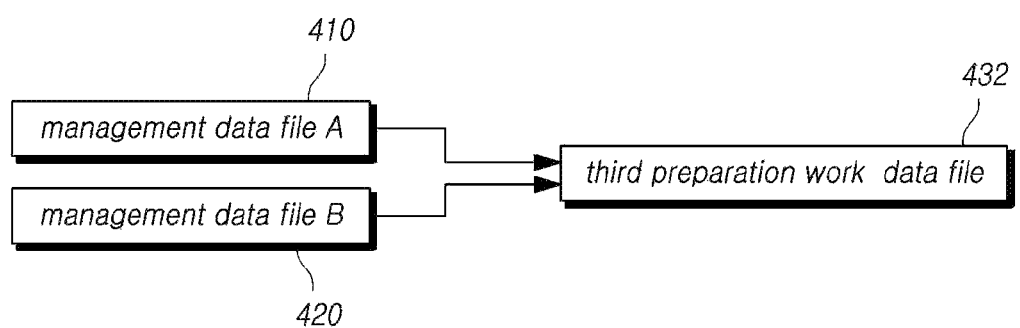

A method of producing a management data file and generating a work data file using the management data file may has an advantage in that this method may produce a smaller number of files than the case of using a work data file. For example, when a desired preparation work is a preparation work (i) of producing a nucleic acid extract, a preparation work (ii) of producing a PCR reaction solution, and a preparation work (iii) of producing a nucleic acid extract and a PCR reaction solution at the same time, three work data files for the three types may need to be prepared. However, in the case of the method of generating a work data file using a management data file, the method may generate a work data file for the preparation work (iii) using the combination of the preparation work (i) and the preparation work (ii) by preparing only two management data files associated with the preparation work (i) of producing a nucleic acid extract and the preparation work (ii) of producing a PCR reaction solution. FIG. 4B is an example of generating a work data file 432 from two management data files 410 and 420.

Figure 4C:
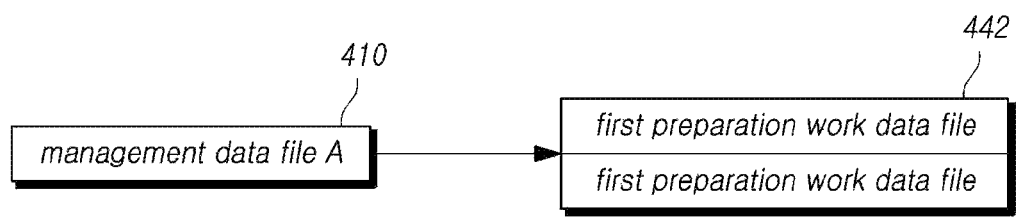
Figure 4D:
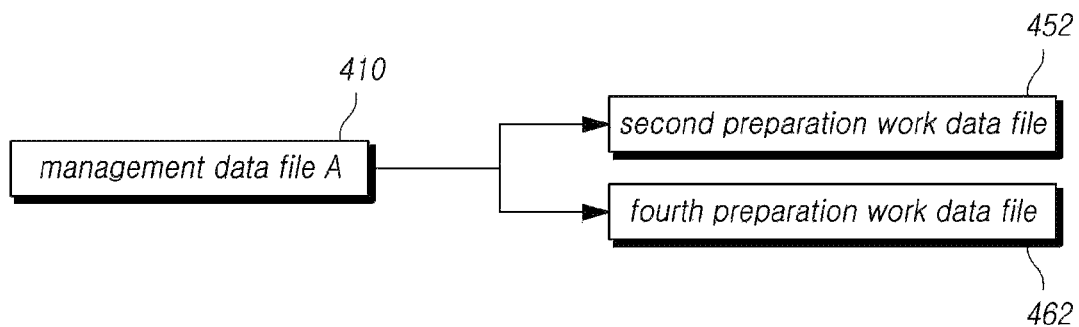

As another example, when a desired preparation work is a preparation work of producing a PCR reaction solution, the work may be performed once or a similar work may be additionally performed once more, according to the number of samples. In the case of using a work data file, two work data files need to be produced by taking into consideration the number of times that the work is performed. Conversely, in the case of using a management data file, two cases may be included in a single management data file, and a suitable work data file may be produced based on the number of samples provided from selection information. FIG. 4C is an example of generating a work data file 442, which repeats the same work, using the single management data file 410.

The management data file is used to manage, store, and transfer information. Accordingly, the management data file may be more efficiently and readily produced than a work processing file that directly controls an instrument based on the information. Also, some of the information included in the management data file may be extracted, and some of the information included in the management data file may be combined with information included in another management data file.

The processor 320 may extract all or some of the work actions in a work list included in a single management data file, and may generate a work data file. That is, two or more work data files 452 and 462 having different work lists may be generated from the single management data file 410 (please refer to FIG. 4D).

Optionally, the processor 320 may extract all or some of the work actions in each of two or more management data files, and may combine the extracted work actions so as to may generate a work data file.

According to an embodiment, a work action may be extracted according to the order of work actions written in a work list, or may be extracted in a different order. Instruction name information, instruction processing information, and the like allocated to the extracted work action may be also extracted.

A work data file may be recognized by a control device, and may need to be capable of performing interaction with a work processing file including an instruction (i.e., an integrated instruction file). According to an embodiment, a work data file may be produced to be suitable to a previously defined frame. According to an embodiment, information included in a work data file may be in a format which can be processed by an integrated instruction file.

Therefore, the method of directly producing a work data file, which has the above-described limitation, may be relatively inefficient. The method and device according to the present disclosure may efficiently provide work data files required for various preparation works using management data files via which information input, management, and processing is relatively easy.

Subsequently, the processor 320 searches for an instruction that matches instruction name information allocated to a work action from an integrated instruction file stored in the integrated instruction file storage 336 in operation S240, according to the order of time-series work actions included in the work data file determined in operation S230.

The integrated instruction file includes all instructions used for implementing all work actions desired to be executed by a preparation instrument, and the processor 320 may perform control such that the work actions are implemented by the preparation instrument using the integrated instruction file. For example, when the preparation instrument is capable of producing a nucleic acid extract and a PCR reaction solution, the integrated instruction file may include all instructions used for implementing all work actions related to the production.

The instructions may include instructions for moving a pipettor that performs pipetting upward and downward, leftward and rightward, or forward and backward, and instructions for dispensing, aspirating, or transferring liquid, by the preparation instrument.

In operation S250, the processor 320 processes the instruction retrieved from the integrated instruction file according to instruction processing information of the determined work data file.

The processor 320 processes retrieved instructions according to the instruction processing information, and controls the preparation instrument such that work actions are implemented by the preparation instrument in operation S260.

According to an embodiment, the memory 330 may include the integrated instruction file storage 336 including an integrated instruction file.

Each instruction included in the integrated instruction file may include unit action variables declared for each instruction.

In the present disclosure, unit actions may be indicated by unit action variables.

A single instruction is designated for related unit actions, and different instructions are configured to include different groups of unit actions.

In the present specification, the term "unit action variables declared for an instruction" may indicate "unit action variables designated to, allocated to, or defined for an instruction" or "unit action variables associated with an instruction".

The work data file/integrated instruction file processor 322 of the processor 320 may search for a matching instruction from the integrated instruction file using instruction name information allocated to a work action of a work data file, may provide instruction processing information connected to the instruction name information to the retrieved instruction, and may perform control such that the corresponding work action is executed by the retrieved instruction.

The instruction may indicate to the processor 320 that a unit action indicated by a corresponding unit action variable needs to be implemented according to variable values of unit action variables defined for an instruction.

The instruction processing information may include unit action variables indicating unit actions included in a work action implemented by the retrieved instruction, and variable values allocated to the unit action variables.

Each instruction included in the integrated instruction file may include unit action variables defined for a corresponding instruction. The processor 320 may process each instruction using unit action variables of which variable values are provided according to the instruction processing information from among unit action variables defined for a corresponding instruction, whereby a corresponding work action is implemented by the preparation instrument.

The integrated instruction file includes a plurality of instructions, and each of the plurality of instructions may be implemented as a combination of a loop that executes one of the plurality of instructions during one time period and a control structure such as if, then, or the like.

Hereinafter, a process of processing an instruction via interaction between a work data file and an integrated instruction file will be described with reference to FIG. 5.

When selection information for executing a first preparation work including time-series work actions A, C, D, and F is received via the display 310, the processor 320 may determine a first work data file 510.

The first work data file 510 includes a first area indicating a work list including time-series work actions A, C, D, and F, a second area indicating instruction name information of instructions I1, I3, I4, and I6 for controlling respective work actions, and a third area indicating unit action variables corresponding to unit actions related to execution of each instruction. Although not illustrated, variable values are allocated to unit action variables, respectively.

In the case of work action A, work action A is implemented by instruction I1, and accordingly, instruction name information I1 is allocated. Also, unit actions associated with instruction I1 are unit action 01, unit action 03, unit action 06, unit action 09, unit action 12, and unit action 15, and a variable value for each unit action variable is allocated.

Figure 5:
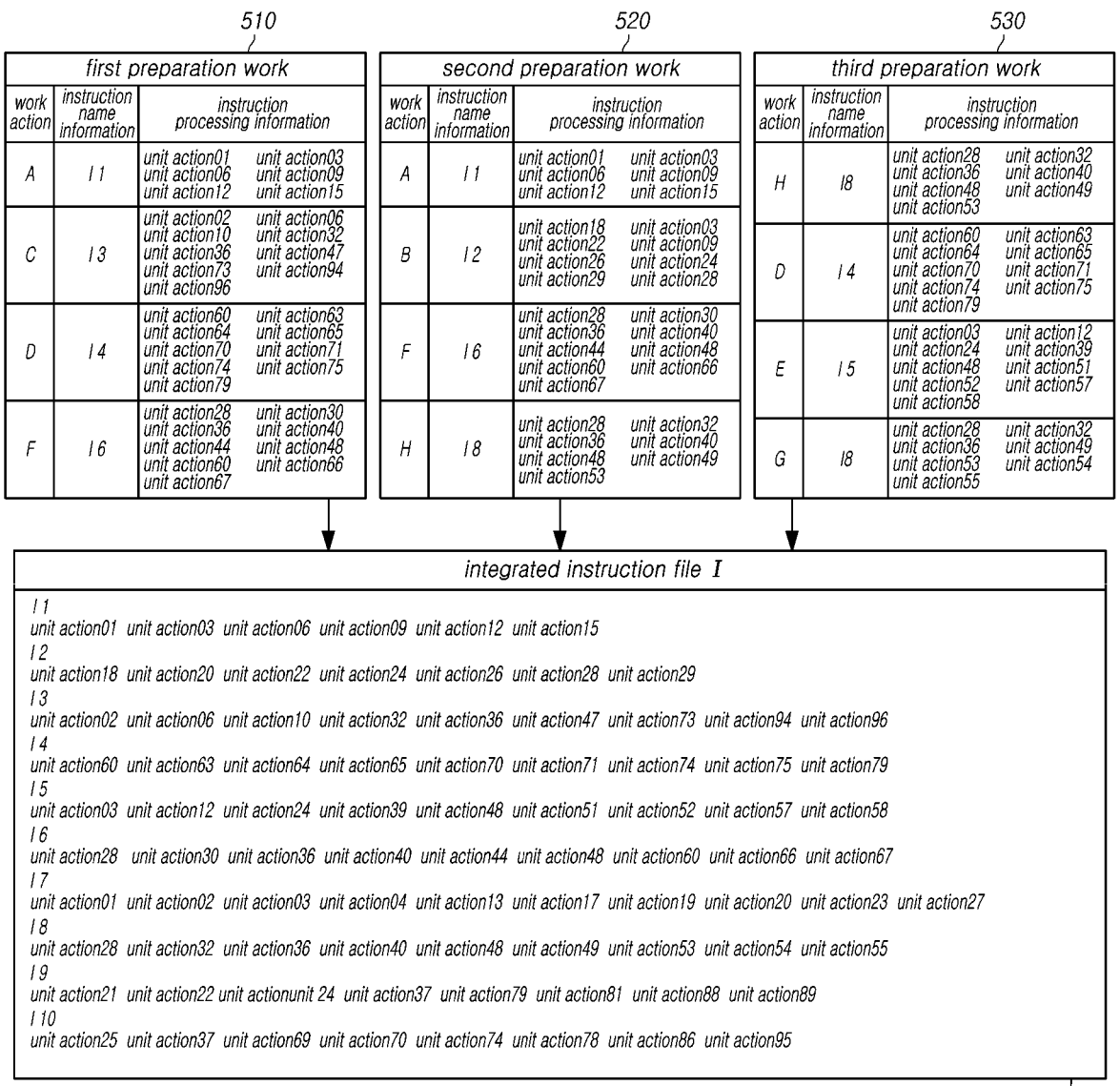
FIG. 5 is a diagram illustrating the configurations of a work data file and an integrated instruction file, and a process of processing an instruction via interaction according to an embodiment of the present disclosure.

In FIG. 5, an integrated instruction file I 540 includes instructions I1 to I10 associated with all work actions desired to be executed by the preparation instrument, and unit action variables for each instruction are defined. For example, variables defined for instruction I1 are unit action 01, unit action 03, unit action 06, unit action 09, unit action 12, and unit action 15.

The processor 320 recognizes that instruction name information allocated to "A", which is a first work action in the first work data file 510 is "I1", and searches for instruction I1 that matches "I1" from instructions I1 to I10 of the integrated instruction file I 540. Subsequently, the processor 320 may provide unit action variable information (i.e., unit action 01, unit action 03, unit action 06, unit action 09, unit action 12, and unit action 15) and variable values thereof, which are the instruction processing information associated with the instruction name information "I1", to the instruction "I1" of the integrated instruction file I 540.

The processor 320 may process the instruction "I1" according to unit action 01, unit action 03, unit action 06, unit action 09, unit action 12, and unit action 15 and variable values thereof, which are provided via the instruction processing information from among unit action variables defined for the instruction "I1", and may perform a control such that work action A is implemented by the preparation instrument.

The processor 320 recognizes that instruction name information allocated to "C ", which is a next work action in the first work data file 510 is "I3", and searches for instruction "I3" that matches "I3" from instructions I1 to I10 of the integrated instruction file I 540. Subsequently, the processor 320 processes the instruction "I3" according to instruction processing information associated with the instruction name information "I3", and enables the instruction "I3" to implement the work action "C". The processor 320 repeats the above-described operation according to the order of work actions in the first work data file, whereby the preparation instrument control device 300 may perform the desired first preparation work.

The integrated instruction file I 540 may be used for performing a preparation work different from the first preparation work.

When selection information for executing a second preparation work including time-series work actions A, B, F, and H is received via the display 310, the processor 320 may determine a second work data file 520 of FIG. 5. It is recognized that the time-series work actions A, B, F, and H in the second work data file 520 are implemented by instructions I1, I2, I6, and I8, respectively. The preparation instrument control device 300 may implement the second preparation work using the second work data file 520 and the integrated instruction file I 540 including the instructions I1, I2, I6, and I8.

Conventionally, in order to execute the first preparation work and the second preparation work, a first work processing file and a second work processing file, each including instructions for executing work actions included in a corresponding preparation work, need to be produced, separately.

The preparation instrument control method (S200) of the present disclosure produces an "integrated instruction file" once, as opposed to producing individual work processing files. Instead, the preparation instrument control method operates a work data file, so as to manage a work list that is changed for each preparation work, and information associated with work actions included in the work list. By using the work data file and the integrated instruction file, various preparation works are efficiently and readily implemented.

At least one instructions in the integrated instruction file I 540 may implement two or more work actions.

For example, referring to information associated with a third work data file 530 for a third preparation work in FIG. 5, the third preparation work includes work actions H, D, E, and G, wherein when the work action H uses instruction I8, the work action D uses instruction I4, and the work action E uses instruction I5, and the work action G uses instruction I8.

According to an embodiment, the processor 320 implements two or more work actions by using different unit action variables from among unit action variables defined for one instruction.

For example, in the integrated instruction file I 540 of FIG. 5, unit action variables including "unit action 28, unit action 32, unit action 36, unit action 40, unit action 48, unit action 49, unit action 53, unit action 54, and unit action 55" are defined for the instruction I8".

The instruction name information allocated to work action "H" in the third work data file 530 is "I8", and connected instruction processing information includes unit action variables including unit action 28, unit action 32, unit action 36, unit action 40, unit action 48, unit action 49, and unit action 53, and variable value information thereof.

The instruction name information allocated to work action "G" is also "I8", but connected instruction processing information includes unit action variables including unit action 28, unit action 32, unit action 36, unit action 49, unit action 53, unit action 54, and unit action 55, and variable value information thereof.

That is, the work action H and the work action G are controlled by the same instruction "I8", but have different combinations of related unit action variables (i.e., unit actions). Accordingly, different work actions are executed.

According to an embodiment, software (or a program) that is in charge of producing, managing, and using a management data file and/or work data file, and software that is in charge of producing, managing, and using an integrated instruction may exist as a single piece of software or may exist as separate pieces of software. According to an embodiment, the (pieces of) software may be executed in one processor, or may be executed in two or more processors.

In some cases, whether desired work actions are accurately arranged need to be identified before a work starts according to a work data file after the work data file is provided according to selection information. Also, a user desires to manually perform an IC dispensing work action (IC_Dispense) included in a work list of the type of extracted detection composition before a preparation work starts, or desires to skip, in the work list, a work action considered to be an unnecessary work action due to the characteristic of the type of detection composition.

The preparation instrument control device 300 of the present disclosure may control the preparation instrument, so as to provide a work window for displaying (notifying of) or editing work actions included in a work data file on the display 310, before starting the preparation work. Via the above, a user may identify the work list, and may selectively perform only a necessary work action.

Also, when work is suspended while the preparation instrument operates, the preparation instrument control device 300 according to the present disclosure may provide state information associated with the suspended work action or may provide a work window for editing a subsequent work action.

For example, in the case in which preparation work actions associated with the type of extracted detection composition are performed, when a clot is detected or an aspirating or dispensing action is abnormally performed in the process of aspiring and dispensing a specimen or a reagent, a separate window may be displayed on the display 310 such that a user identifies the location of a sample and dispenses the accurate volume of the sample to a sample tube. Also, the suspended work action is indicated in the work list of the work data file, and work action options are provided such that the remaining work actions are performed, whereby only necessary work actions are performed.

The processor 320 according to the present disclosure may further perform generating a setting data file using the selection information of operation S220.

According to an embodiment, the processor 320 may include the setting data file generator 326 that generates a setting data file.

The setting data file includes selection information including the type of a preparation work based on the type of detection composition, the type of target nucleic acid molecule desired to be detected using a test product, and information associated with tools (consumables) required for performing a work by the preparation instrument (a labware containing an extracted nucleic acid, a tube or plate containing a PCR reaction mixture, and the like).

In addition, selection information, such as additional information (extraction kit, PC, NC, cartridge count, and the like) that is set in advance or that is manually input by a user via a barcode or an input device such as a mouse, and the like, may be further included.

Information associated with the generated setting data file may be information associated with a work data file which is to be determined (or which has been determined), or may be utilized as a unit action variable, a variable value, or the like required for processing an instruction using an integrated instruction file.

For example, the setting data file includes information associated with the type of detection composition based on received selection information, a product for a test, and the type of target nucleic acid molecule that a user desires to detect using the product for a test, whereby the setting data file may support information for determining a corresponding work data file.

The processor 320 may process selection information recorded in the setting data file via interoperation with an interoperated instruction file.

According to an embodiment, when an instruction is processed according to instruction processing information according to selection information recorded in the setting data file, a processing sequence of unit action variables may be changed. According to an embodiment, in selection information based on a user's intention, variable values may be differently allocated according to tools (consumables). For example, in the case of a sample labware, variable values may be differently allocated based on the type of tube.

In the case of a variable indicating an action of aspirating a specimen from a specimen tube from among variables indicating unit actions of a work action, the volume of an aspirated specimen needs to be changed based on the type of tube.

Therefore, in the case in which unit actions are performed using tools, when instruction processing is performed according to instruction processing information, the processing sequence of unit action variables may be changed based on the type of tool, or variable values need to be processed differently based on selection information.

Although specific parts of the present disclosure have been described in detail, it is apparent to those skilled in the art that the detailed-descriptions are merely preferable embodiments, and do not limit the scope of the present disclosure. Therefore, it should be understood that the actual scope of the present disclosure is defined by the claims attached herein and the equivalent thereto.

The invention claimed is:

1. A method of controlling a preparation instrument which prepares a detection composition used for detecting a target nucleic acid molecule in a specimen, the method comprising:
   displaying a plurality of option fields comprising a type of detection composition and a type of target nucleic acid molecule desired to be detected on a display so as to determine a desired detection composition, wherein the detection composition includes a nucleic acid extract and a reaction solution for nucleic acid amplification;
   receiving user selection information from each of the plurality of option fields;
   determining a work data file based on the selection information, wherein the work data file comprises a work list comprising time-series work actions required for preparing the nucleic acid extract and/or a work list comprising time-series work actions required for preparing the reaction solution for nucleic acid amplification, and comprises instruction name information and instruction processing information used for implementing the work actions in the preparation instrument;
   searching for an instruction that matches the instruction name information allocated to a work action from an integrated instruction file, according to the order of the work actions included in the determined work data file, wherein the integrated instruction file comprises all instructions used for implementing all work actions that are desired to be operated in the preparation instrument, and the instructions comprise instructions for moving a pipettor, which performs pipetting in the preparation instrument, upward and downward, leftward and rightward, and forward and backward, and for dispensing, aspirating, or transferring a liquid; and
   performing control such that the retrieved instructions are processed according to the instruction processing information and the work actions are implemented in the preparation instrument.

2. The method as claimed in claim 1, wherein the step of determining the work data file comprises:
   generating the work data file using the selection information and one or more management data files selected based on the selection information, wherein the management data files are classified and stored according to a type of detection composition and a type of target nucleic acid molecule, and comprises work actions included in the work data file required according to the selection information, and instruction name information and instruction processing information associated with each work action.

3. The method as claimed in claim 2, wherein the step of generating the work data file comprises:
   generating the work data file by extracting some or all work actions included in a single management data file, or generating the work data file by extracting some or all work actions included in each of the two or more management data files and combining the extracted work actions.

4. The method as claimed in claim 1, wherein the instruction processing information comprises:
   unit action variables indicating unit actions of work actions implemented by the retrieved instructions and variable values allocated to the unit action variables.

5. The method as claimed in claim 1, wherein each instruction in the integrated instruction file comprises unit action variables defined for a corresponding instruction, the unit action variables indicate unit actions of a work action implemented by an instruction, and each instruction is processed using unit action variables of which variable values are provided according to the instruction processing information from among unit action variables defined for each instruction.

6. The method as claimed in claim 1, wherein at least one instructions in the integrated instruction file implements two or more work actions.

7. The method as claimed in claim 6, wherein unit action variables to be used from among unit action variables defined for the at least one instructions are set to be different, such that two or more work actions are implemented.

8. The method as claimed in claim 1, further comprising: displaying, on the display, a work window for displaying or editing work actions included in the work data file before controlling the preparation instrument.

9. The method as claimed in claim 1, wherein, when work is suspended while the preparation instrument operates, the method further comprises displaying, on the display, a work window for displaying state information of the suspended work action or editing a subsequent work action.

10. The method as claimed in claim 1, further comprising: generating a setting data file in which the selection information is recorded, wherein the selection information recorded in the setting data file is processed via interoperation with the integrated instruction file.

11. A device for controlling a preparation instrument which prepares a detection composition used for detecting a target nucleic acid molecule in a specimen, the device comprising:
a display, a processor, and a memory,
wherein the processor is configured to perform:
displaying a plurality of option fields comprising a type of detection composition and a type of target nucleic acid molecule desired to be detected on the display so as to determine a desired detection composition, wherein the detection composition comprises a nucleic acid extract and a reaction solution for nucleic acid amplification;
receiving user selection information from each of the plurality of option fields so as to determine a work data file based on the selection information, wherein the work data file comprises a work list comprising time-series work actions required for preparing the nucleic acid extract and/or a work list comprising time-series work actions required for preparing the reaction solution for nucleic acid amplification, and comprises instruction name information and instruction processing information used for implementing the work actions in the preparation instrument;
searching for an instruction that matches the instruction name information allocated to a work action from an integrated instruction file, according to the order of the work actions included in the determined work data file, wherein the integrated instruction file comprises all instructions used for implementing all work actions that are desired to be operated in the preparation instrument, and the instructions comprise instructions for moving a pipettor, which performs pipetting in the preparation instrument, upward and downward, leftward and rightward, and forward and backward, and for dispensing, aspirating, or transferring a liquid; and
performing control such that the retrieved instructions are processed according to the instruction processing information and the work actions are implemented in the preparation instrument.

12. The device as claimed in claim 11, wherein the memory is configured to store a management data file comprising work actions included in a work data file required according to selection information, and instruction name information and instruction processing information associated with each work action, wherein the management data file is classified and stored according to a type of detection composition and a type of target nucleic acid molecule; and
the processor is configured to generate the work data file using the selection information and one or more management data files selected based on the selection information, and implements determining the work data file.

13. The device as claimed in claim 12, wherein the processor is configured to generate the work data file by extracting some or all work actions included in a single management data file, or to generate the work data file by extracting some or all work actions included in each of the two or more management data files and combining the extracted work actions.

14. The device as claimed in claim 11, wherein the instruction processing information comprises:
unit action variables indicating unit actions of work actions implemented by the retrieved instructions and variable values allocated to the unit action variables.

15. The device as claimed in claim 11, wherein each instruction in the integrated instruction file comprises unit action variables defined for a corresponding instruction, and the unit action variables indicate unit actions of a work action implemented by an instruction; and
the processor is configured to process each instruction using unit action variables of which variable values are provided according to the instruction processing information from among unit action variables defined for each instruction.

16. The device as claimed in claim 11, wherein the processor is configured to enable at least one instructions in the integrated instruction file to implement two or more work actions.

17. The device as claimed in claim 16, wherein the processor is configured to set unit action variables, which are to be used from among unit action variables defined for the at least one instructions, to be different, such that two or more work actions are implemented.

18. The device as claimed in claim 11, wherein the processor is configured to display, on the display, a work window for displaying or editing work actions included in the work data file before controlling the preparation instrument.

19. The device as claimed in claim 11, wherein, when work is suspended while the preparation instrument operates, the processor is configured to display, on the display, a work window for displaying state information of the suspended work action or editing a subsequent work action.

20. The device as claimed in claim 11, wherein the processor is configured to generate a setting data file in which the selection information is recorded, and to process the selection information recorded in the setting data file via interoperation with the integrated instruction file.

* * * * *